United States Patent
Goldiner

(10) Patent No.: US 11,257,577 B1
(45) Date of Patent: Feb. 22, 2022

(54) METHOD, APPARATUS, AND COMPUTER PROGRAM PRODUCT FOR THE GENERATION AND USE OF CARDIOLOGY REPORTING DIAGRAMS

(71) Applicant: Change Healthcare Holdings, LLC, Nashville, TN (US)

(72) Inventor: Uri Goldiner, Tel Aviv (IL)

(73) Assignee: CHANGE HEALTHCARE HOLDINGS, LLC, Charlotte, NC (US)

(*) Notice: Subject to any disclaimer, the term of this patent is extended or adjusted under 35 U.S.C. 154(b) by 265 days.

(21) Appl. No.: 16/368,937

(22) Filed: Mar. 29, 2019

Related U.S. Application Data

(60) Provisional application No. 62/770,572, filed on Nov. 21, 2018.

(51) Int. Cl.
| | |
|---|---|
| *G16H 15/00* | (2018.01) |
| *G16H 10/60* | (2018.01) |
| *G16H 30/40* | (2018.01) |
| *G16H 40/20* | (2018.01) |

(52) U.S. Cl.
CPC ............ *G16H 15/00* (2018.01); *G16H 10/60* (2018.01); *G16H 30/40* (2018.01); *G16H 40/20* (2018.01)

(58) Field of Classification Search
USPC ........................................................ 705/2–3
See application file for complete search history.

(56) References Cited

U.S. PATENT DOCUMENTS

| | | | | |
|---|---|---|---|---|
| 6,684,276 | B2 * | 1/2004 | Walker ................... | G16H 15/00 710/73 |
| 10,503,867 | B1 * | 12/2019 | Walker ................... | G06F 40/106 |
| 2008/0103833 | A1 * | 5/2008 | Miglietta ............... | G16H 20/00 705/3 |
| 2016/0007879 | A1 * | 1/2016 | Gonzalez ............. | A61B 5/0537 600/306 |
| 2016/0217586 | A1 * | 7/2016 | Dickrell, III ........... | G06T 7/168 |

OTHER PUBLICATIONS

Xiao, et al., "An Automated Segmentation Method for Lung Parenchyma Image Sequences Based on Fractal Geometry and Convex Hull Algorithm", Applied Science May 21, 2018, pp. 1-16 (Year: 2018).*

* cited by examiner

*Primary Examiner* — Amber A Misiaszek
(74) *Attorney, Agent, or Firm* — Meunier Carlin & Curfman LLC

(57) ABSTRACT

A method, apparatus, and computer program product are provided herein to facilitate clinical diagram generation and interaction. Methods may include: providing for display of a clinical diagram, where the clinical diagram includes a depiction of the vascular system, where vessels of the vascular system include a plurality of vessel segments, where each segment is formed from a pair of cardinal splines and end lines between adjacent ends of the cardinal splines; providing for generation of a clinical report associated with the clinical diagram; and populating the clinical report in response to user input received in the clinical diagram, where the user input is indicative of at least one clinical finding and a location corresponding to the user input based on a segment selected by the user input.

20 Claims, 12 Drawing Sheets

METHOD, APPARATUS, AND COMPUTER PROGRAM PRODUCT FOR THE GENERATION AND USE OF CARDIOLOGY REPORTING DIAGRAMS

CROSS-REFERENCE TO RELATED APPLICATIONS

This application claims priority to U.S. Provisional Application Ser. No. 62/770,572, filed on Nov. 21, 2018, the contents of which are hereby incorporated by reference in their entirety.

TECHNOLOGICAL FIELD

The present invention relates to an apparatus, method, and computer program product for generating a clinical diagram for use in the generation of a clinical report, and more particularly, to a method of generating and using a clinical diagram to facilitate efficient generation of clinical reports.

BACKGROUND

Clinical reporting is a fundamental practice in medicine, whereby a physician examines a patient and generates a clinical report based on the findings. Clinical diagrams may be used to graphically depict a patient's anatomy, and may provide a tool for physicians to indicate locations of clinical findings. Clinical diagrams and reports may be generated by a physician for a patient's medical record and may be used for current diagnoses and future treatment. The generation of clinical diagrams and reports must be accurate to provide the proper care and benefit to a patient. However, the generation of clinical diagrams and reports can be laborious and inefficient. When tasks are more cumbersome, performing the tasks becomes more tedious and more prone to issues. With the manual generation of clinical reports and diagrams, there is greater likelihood of discrepancies and issues between the report and the diagram, or information omitted from one or the other due to the duplicative nature of some of the elements of a report relative to a diagram. Electronic clinical reports and diagrams may be more user friendly and may be more efficient; however, such reports and diagrams may still suffer from user interface issues and complexities.

BRIEF SUMMARY

Embodiments of the disclosure include an apparatus for facilitating clinical reporting having at least one processor and at least one non-transitory memory including computer program code instructions stored thereon. The computer program code instructions are configured to, when executed, cause the apparatus to at least: provide for display of a clinical diagram, where the clinical diagram includes a depiction of a vascular system, where vessels of the vascular system include a plurality of vessel segments, and each segment is formed from a pair of cardinal splines and end lines between adjacent ends of the cardinal splines; provide for generation of a clinical report associated with the clinical diagram; and populate the clinical report in response to user input received in the clinical diagram, where the user input is indicative of at least one clinical finding on the depiction of the vascular system, where the clinical report is populated with the at least one clinical finding and a location corresponding to a segment selected by the user. Each segment of the vascular system may include unique identifying information, where the identifying information includes a position of the segment within the vascular system, and a function of the segment within the vascular system. The at least one clinical finding may include at least one of a blockage, a stent placement, or a connector between vessels.

According to some embodiments, the clinical diagram is a first clinical diagram from among a plurality of available clinical diagrams, where the apparatus is further caused to: provide a user interface to facilitate selection of a clinical diagram from among the plurality of available clinical diagrams; and receive a selection of the first clinical diagram. The apparatus of some embodiments may be caused to: receive user input corresponding to a modification of the clinical diagram, where the modification includes a new vessel or connector to be added to the clinical diagram; receive an indication of placement of the new vessel or connector in the clinical diagram; and apply a connectivity algorithm to the new vessel or connector to join the new vessel or connector to an existing segment. The connectivity algorithm may use proximity of the new vessel or connector to existing segments and a hierarchy of existing segments to establish an existing segment to which the new vessel or connector is joined. Causing the apparatus to join the new vessel or connector to an existing segment may include causing the apparatus to: convert a three point cardinal spline of the pair of cardinal splines of the existing segment to a four point spline, replacing a middle control point of the three point cardinal spline with two points, and joining ends of the two splines forming the new vessel or connector to the two points.

Embodiments provided herein may include a computer program product including at least one non-transitory computer-readable storage medium having computer-executable program code instructions stored therein. The computer-executable program code instructions may include program code instructions to: provide for display of a clinical diagram, where the clinical diagram includes a depiction of a vascular system, where vessels of the vascular system include a plurality of vessel segments, where each segment may be formed from a pair of cardinal splines and end lines between adjacent ends of the cardinal splines; provide for generation of a clinical report associated with the clinical diagram; and populate the clinical report in response to user input received in the clinical diagram, where the user input is indicative of at least one clinical finding on the depiction of the vascular system, where the clinical report is populated with the at least one clinical finding and a location corresponding to the user input based on a segment selected by the user input. Each segment of the vascular system may include unique identifying information, where the identifying information includes a position of the segment within the vascular system and a function of the segment within the vascular system. The at least one clinical finding includes at least one of a blockage, a stent placement, or a connector between vessels.

According to some embodiments, the clinical diagram may be a first clinical diagram from among a plurality of available clinical diagrams, where the computer program product further includes program code instructions to: provide a user interface to facilitate selection of a clinical diagram from among the plurality of available clinical diagrams; and receive a selection of the first clinical diagram. The computer program product may optionally include program code instructions to: receive user input corresponding to a modification of the clinical diagram, where the modification includes a new vessel or connector to be added to the clinical diagram; receive an indication of placement of the new vessel or connector in the clinical diagram; and apply a connectivity algorithm to the new vessel or connector to join the new vessel or connector to an existing segment. The connectivity algorithm may use proximity of the new vessel or connector to existing segments and a hierarchy of existing segments to establish an existing segment to which the new vessel or connector is joined. The program code instructions to join the new vessel or connector to an existing segment may include program code instructions to: convert a three point cardinal spline of the pair of cardinal splines of the existing segment to a four point spline, replacing a middle control point of the three point cardinal spline with two points; and joining ends of the two splines forming the new vessel or connector to the two points.

Embodiments described herein may provide a method. Methods may include: providing for display of a clinical diagram, where the clinical diagram includes a depiction of the vascular system, where vessels of the vascular system include a plurality of vessel segments, where each segment is formed from a pair of cardinal splines and end lines between adjacent ends of the cardinal splines; providing for generation of a clinical report associated with the clinical diagram; and populating the clinical report in response to user input received in the clinical diagram, where the user input is indicative of at least one clinical finding and a location corresponding to the user input based on a segment selected by the user input. Each segment of the vascular system may include unique identifying information, where the identifying information includes a position of the segment within the vascular system and a function of the segment within the vascular system, the at least one clinical finding may include at least one of a blockage, a stent placement, or a connector between vessels.

According to some embodiments, the clinical diagram may be a first clinical diagram from among a plurality of available clinical diagrams, where methods may include: providing a user interface to facilitate selection of a clinical diagram from among the plurality of available clinical diagrams; and receiving a selection of the first clinical diagram. Methods may include receiving user input corresponding to a modification of the clinical diagram, where the modification includes a new vessel or connector to be added to the clinical diagram; receiving an indication of placement of the new vessel or connector in the clinical diagram; and applying a connectivity algorithm to the new vessel or connector to join the new vessel or connector to an existing segment. The connectivity algorithm may use proximity of the new vessel or connector to existing segments and a hierarchy of existing segments to establish an existing segment to which the new vessel or connector is joined.

BRIEF DESCRIPTION OF THE DRAWINGS

Figure 1:
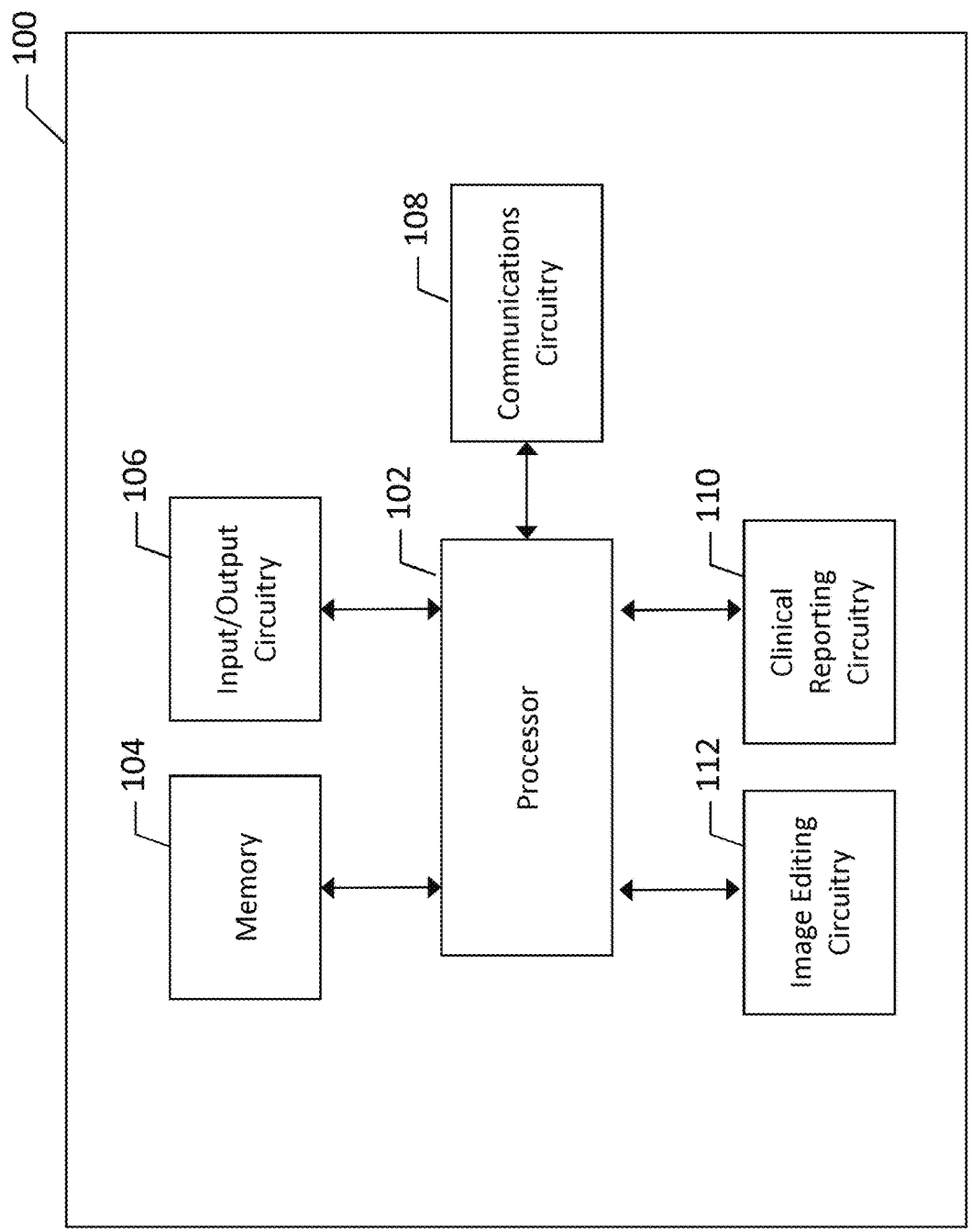
Figure 2:
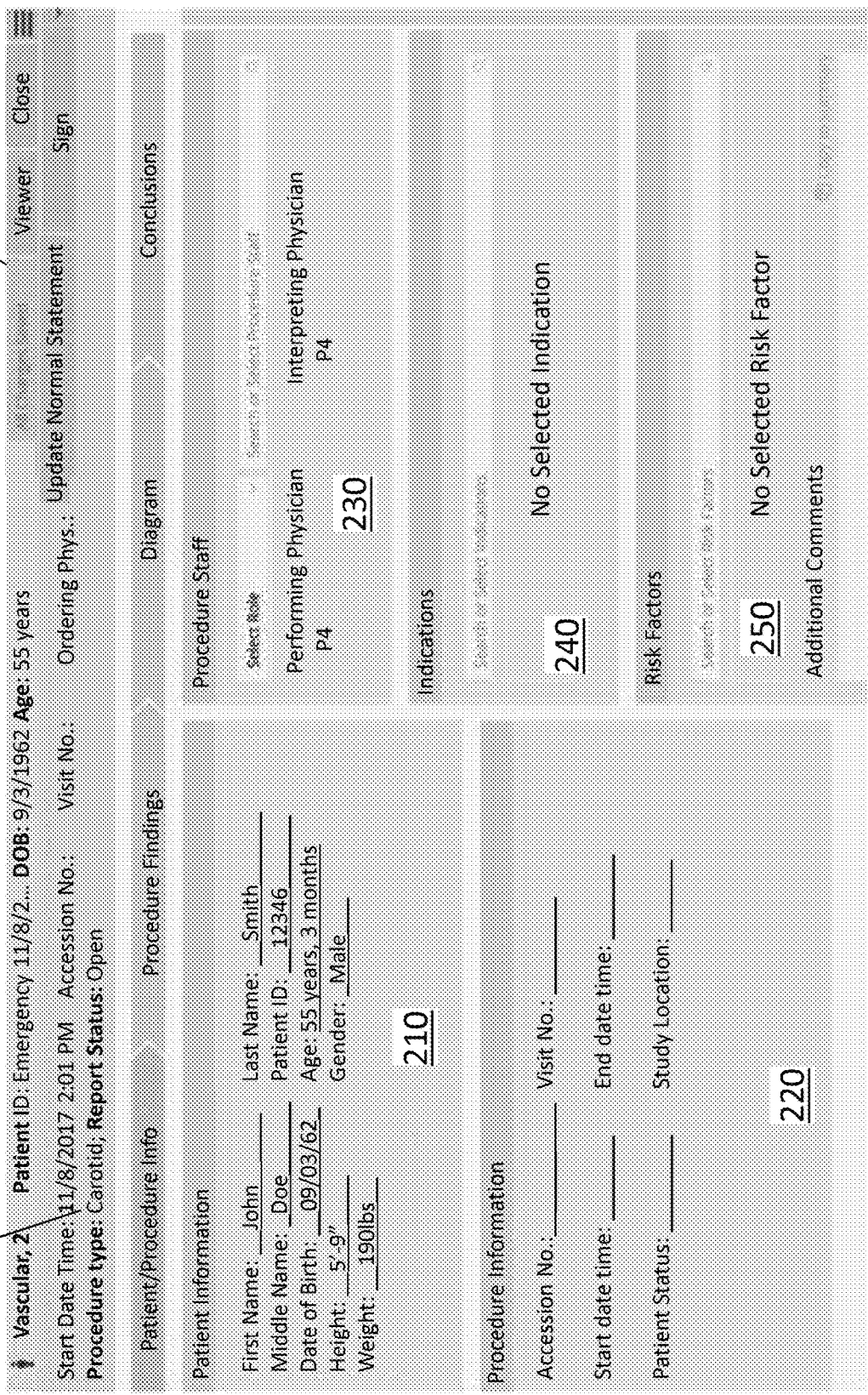
Figure 3:
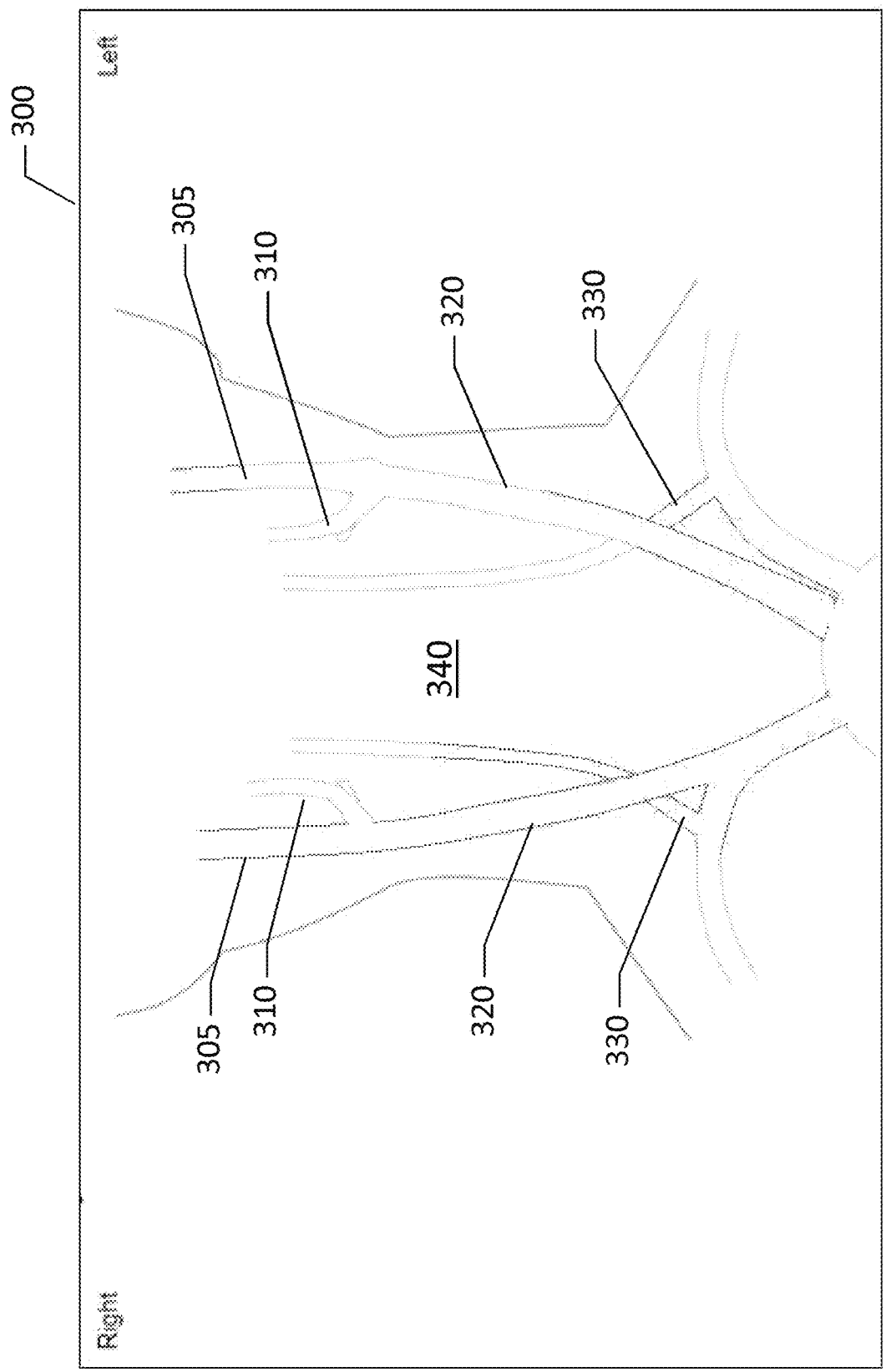
Figure 4:
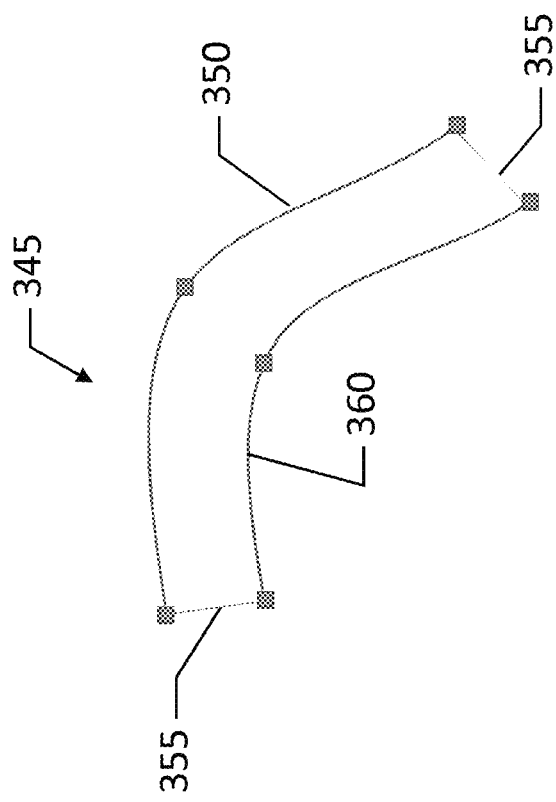
Figure 5:
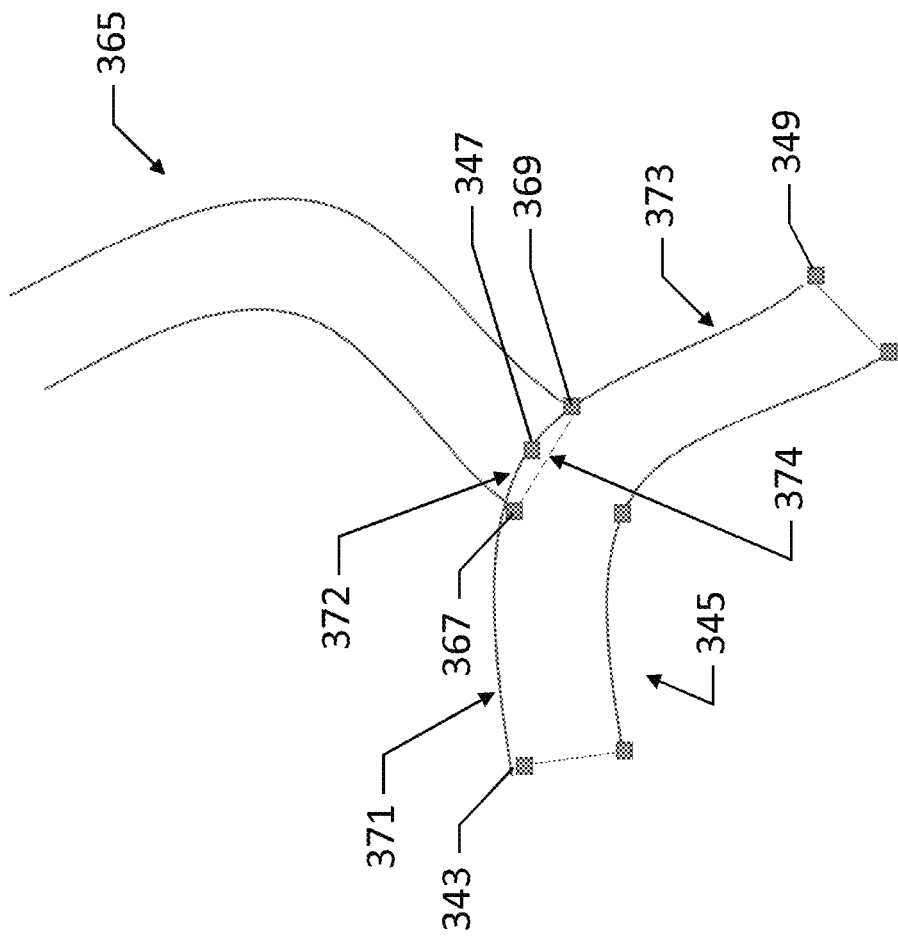
Figure 6:
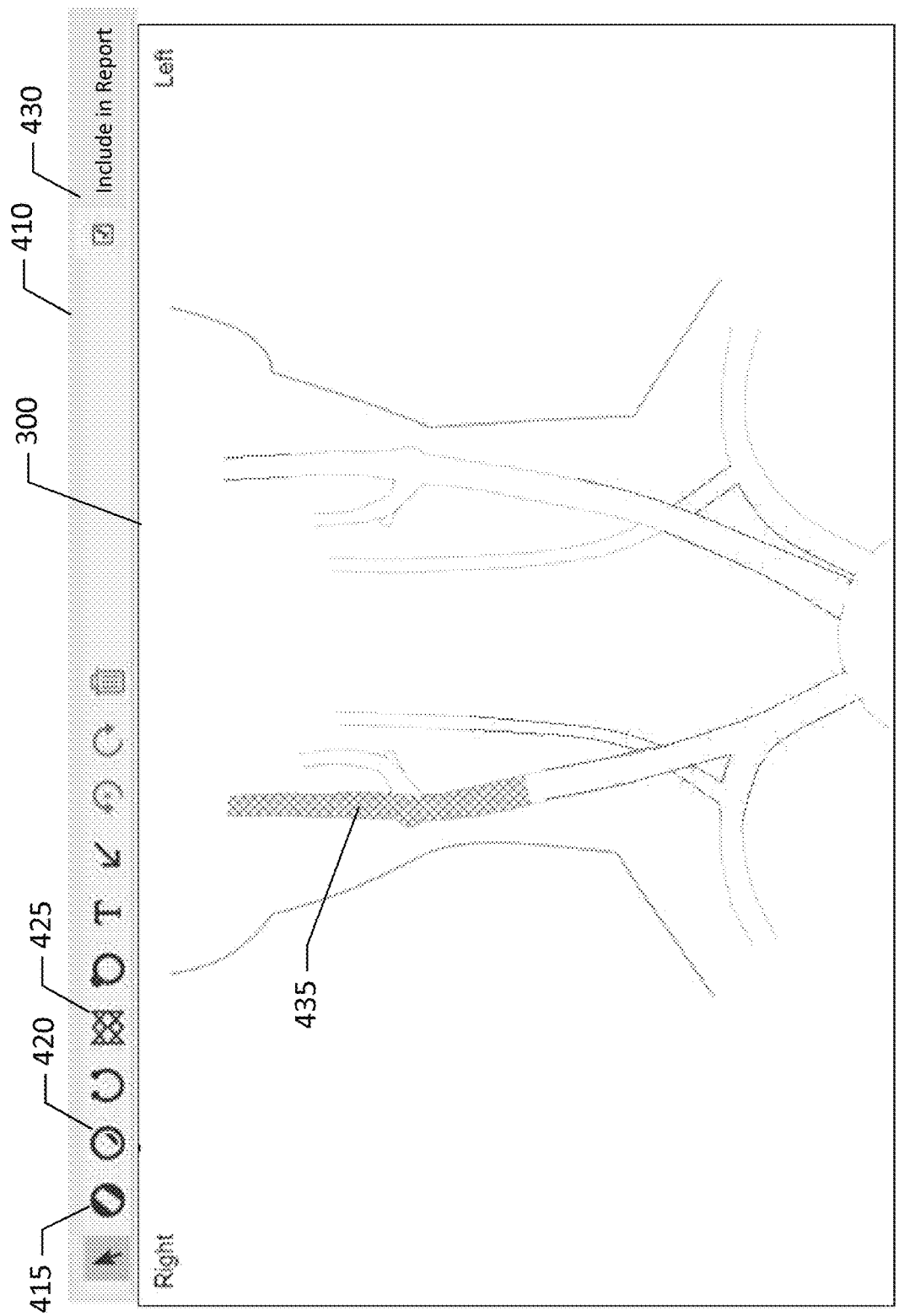
Figure 7:
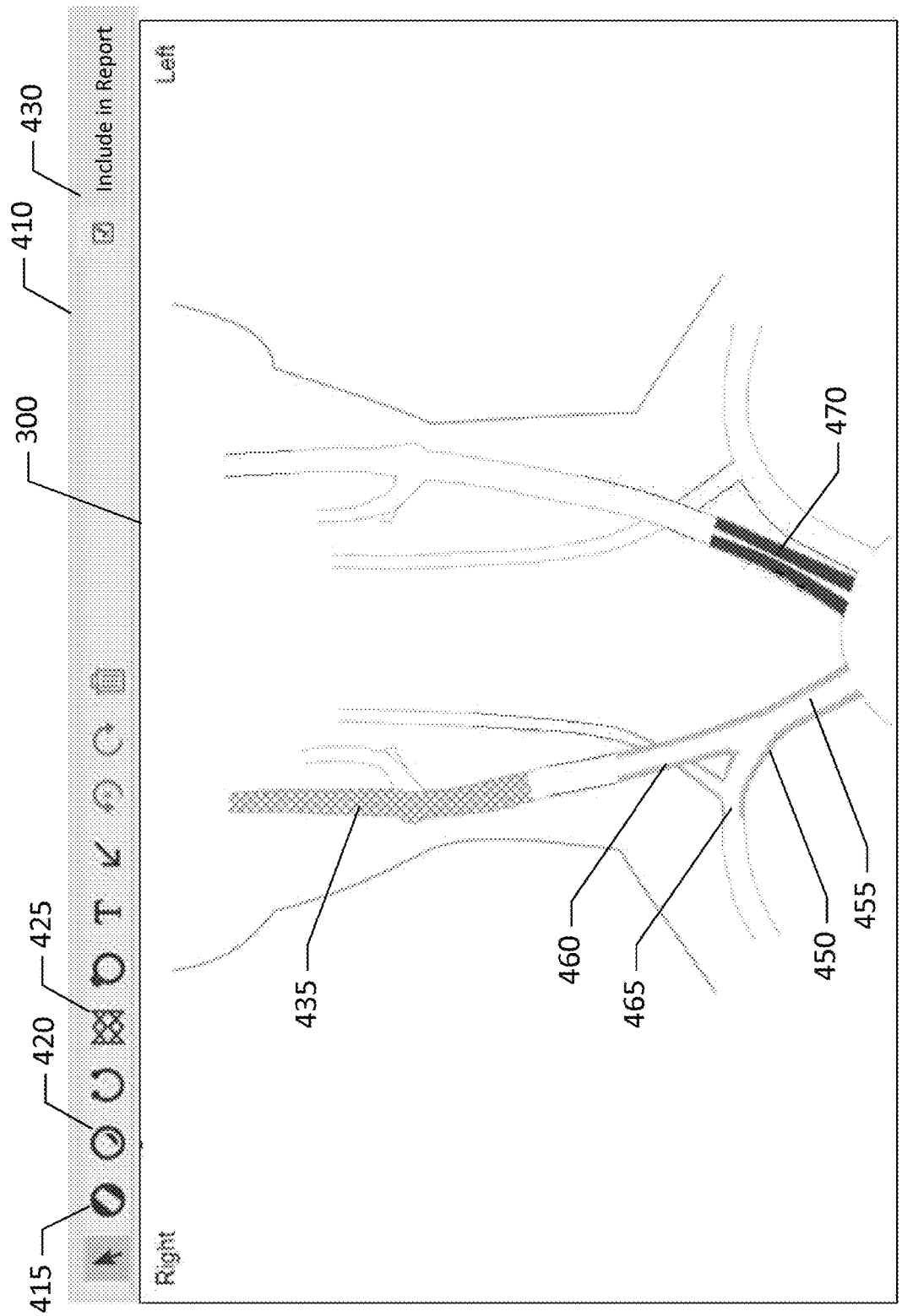
Figure 8:
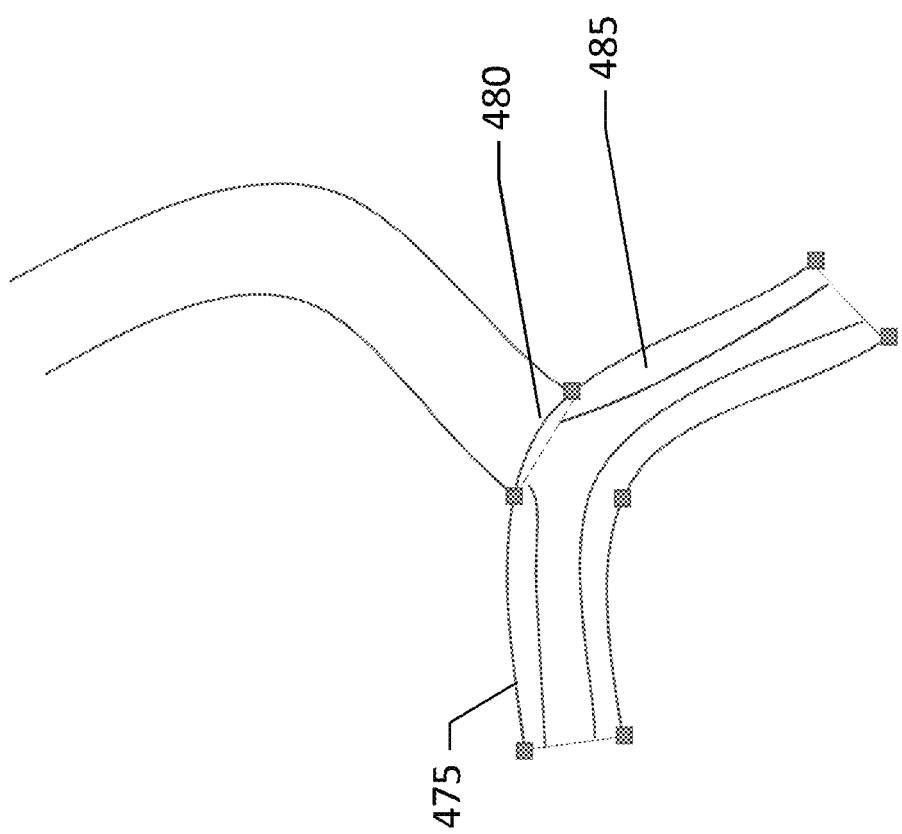
Figure 9:
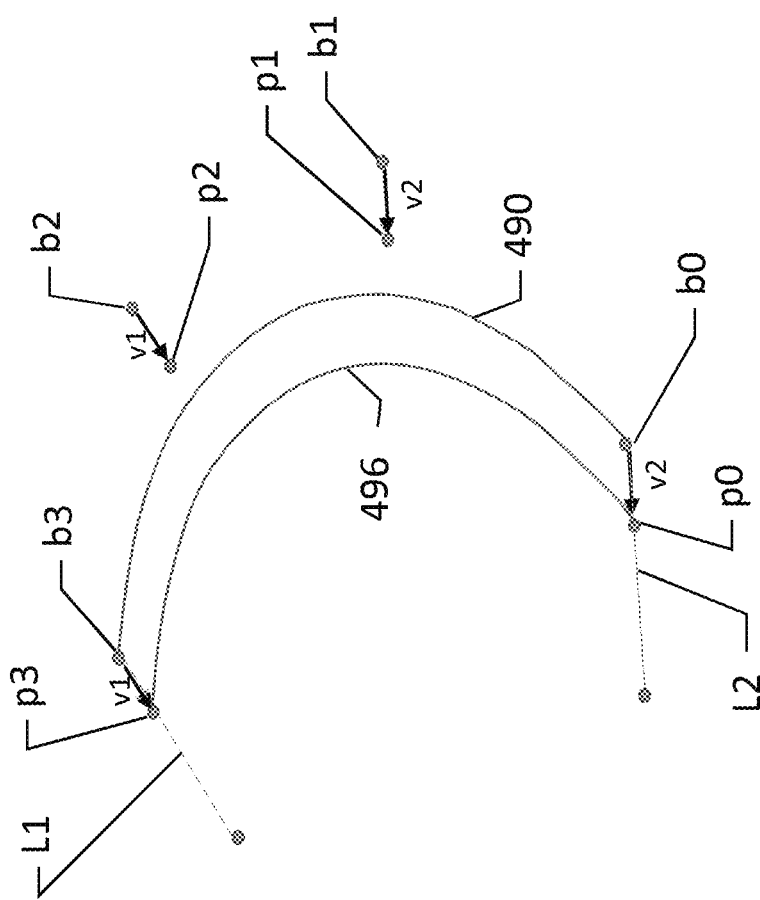
Figure 10:
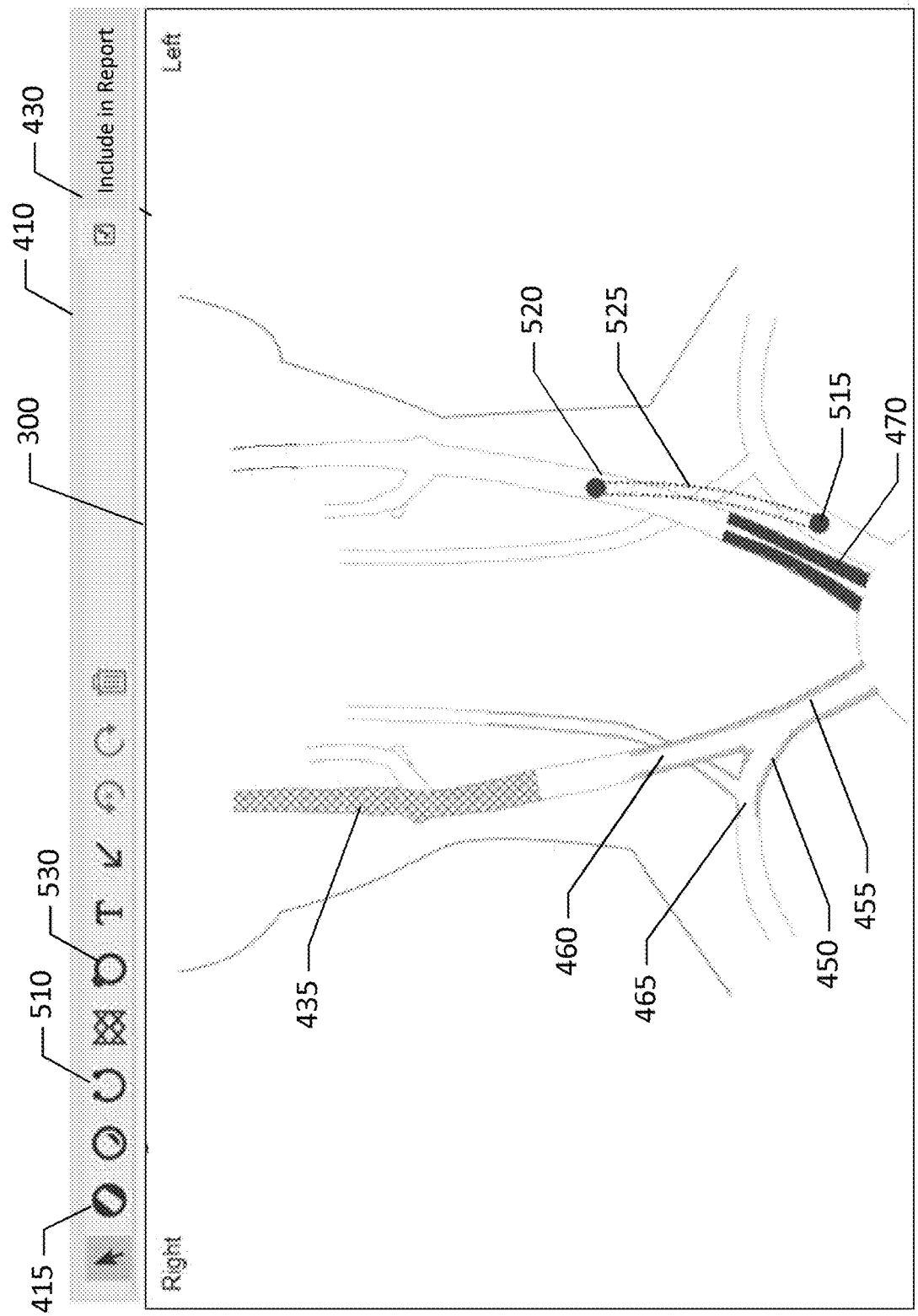
Figure 11:
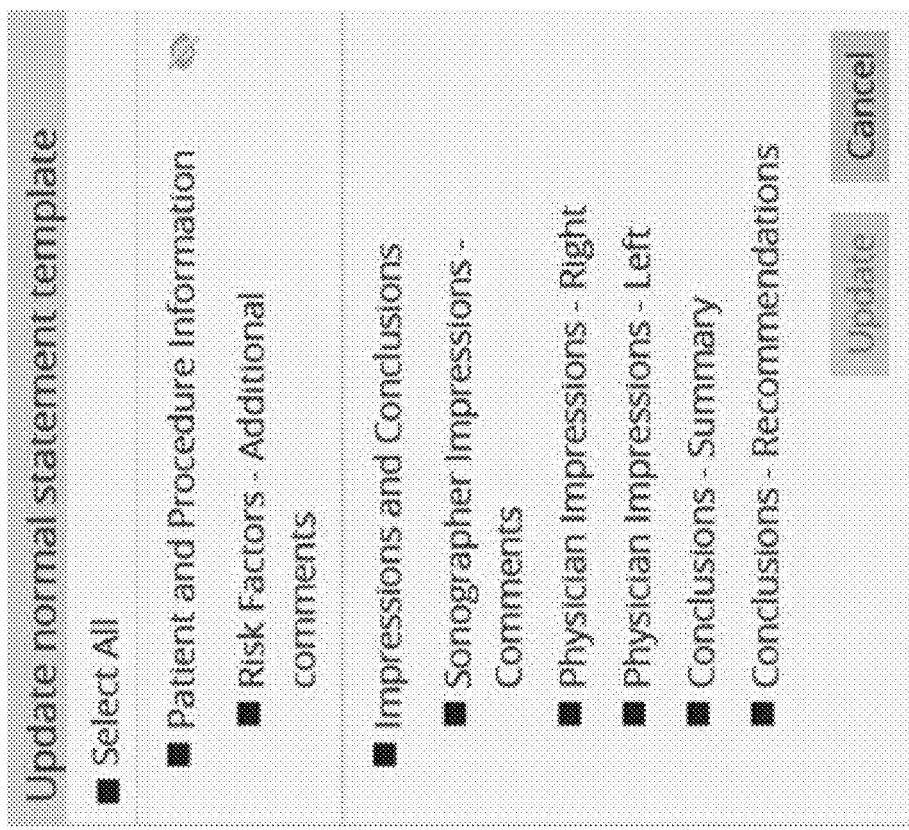
Figure 12:

Having thus described the invention in general terms, reference will now be made to the accompanying drawings, which are not necessarily drawn to scale, and wherein:

FIG. 1 illustrates a diagram of an example embodiment of an apparatus or system for implementing example embodiments of the present disclosure;

FIG. 2 depicts a clinical report template according to an example embodiment of the present disclosure;

FIG. 3 illustrates a clinical diagram of the carotid vascular system according to an example embodiment of the present disclosure;

FIG. 4 illustrates a vascular segment generated using cardinal splines according to an example embodiment of the present disclosure;

FIG. 5 illustrates a joining operation of two vascular segments using a connectivity algorithm according to example embodiments described herein;

FIG. 6 illustrates an interactive clinical diagram of the carotid vascular system and includes stent placement according to an example embodiment of the present disclosure;

FIG. 7 illustrates the interactive clinical diagram of FIG. 6 including the placement of plaque within arteries according to an example embodiment of the present disclosure;

FIG. 8 illustrates the inclusion of plaque within a vessel segment according to an example embodiment of the present disclosure;

FIG. 9 depicts the calculation and placement of plaque within a vessel according to an example embodiment of the present disclosure;

FIG. 10 illustrates the interactive clinical diagram of FIG. 6 including the placement of a graft according to an example embodiment of the present disclosure;

FIG. 11 depicts an example embodiment of a menu for selecting normal statements for a clinical report according to an example embodiment described herein; and FIG. 12 illustrates a clinical report generated according to example embodiments of the present disclosure.

DETAILED DESCRIPTION

A method, apparatus and computer program product are provided in accordance with example embodiments of the present invention to provide improved systems for generating medical reports and corresponding reporting diagrams. Provided herein is a system that generates reporting diagrams corresponding to text reports, and conversely can generate text reports based on reporting diagram input. In this manner, embodiments of the present disclosure diagram biological systems such as the vascular system and provide a visual presentation of clinical finding data in a manner that links graphical depictions of the diagram with findings in a text clinical report.

Example embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Medical treatment of the human body is often performed based on symptoms and diagnostic measurements of properties of the patient, such as blood pressure. However, advances in medical technology have enabled treatment of patients to be performed based on patient-specific diagraming of a patient's biological systems. For example, patient-specific cardiovascular diagraming as described herein may be used to visually represent the cardiovascular system of a patient. Cardiovascular system details that are unique to an individual patient may be used to provide better treatment to a patient through a more thorough understanding of a patient's unique system. Beyond identifying that a patient may have artery blockages, stents, or grafts among other cardiovascular system specifics in a textual report, embodiments described herein may provide a graphical user interface to depict a diagram of the cardiovascular system of a patient and to depict patient-specific attributes within the cardiovascular system that are associated with findings in the clinical report for the patient.

Embodiments described herein provide patient-specific clinical diagraming of biological systems of a patient, and in particular, modeling of cardiovascular systems or portions thereof. The diagrams generated through example embodiments may be used for clinical reporting purposes and may facilitate technician and physician workflow and enhance clinical support. Embodiments may enable technicians and physicians to use a diagram/model-driven workflow to enhance or replace existing report driven workflows.

FIG. 1 illustrates a block diagram of an apparatus 100 in accordance with some example embodiments. The apparatus 100 may be any computing device capable of implementing improved techniques for creating a clinical diagram for viewing and reporting clinical findings as described herein. For example, the apparatus 100 may be implemented as a computing device executing one or more applications for generating, receiving, processing, and outputting clinical reports and diagrams. The apparatus 100 implements hardware and software that serve to generate clinical reporting diagrams from clinical reports and to generate clinical reports based on clinical reporting diagram input.

The apparatus 100 may be implemented as a standalone or rack-mounted server, a desktop computer, a laptop computer, a personal digital assistant, a tablet computer, a netbook computer, a mobile device, or the like. Accordingly, it will be appreciated that the apparatus 100 may comprise devices, hardware, and the like configured to implement and/or otherwise support implementation of various example embodiments described herein.

It should be noted that the components, devices or elements illustrated in and described with respect to FIG. 1 below may not be mandatory and thus some may be omitted in certain embodiments. Additionally, some embodiments may include further or different components, devices or elements beyond those illustrated in and described with respect to FIG. 1.

As illustrated in FIG. 1, an apparatus 100 may include a processor 102, a memory 104, input/output circuitry 106, communications circuitry 108, clinical reporting circuitry 110, and image editing circuitry 112. The apparatus 100 may be configured to generate a clinical diagram based upon specific user instruction, or to create a clinical diagram based on text input received in a corresponding clinical report as described further below. Although these components 102-112 are described with respect to functional limitations, it should be understood that the particular implementations necessarily include the use of particular hardware. It should also be understood that certain of these components 102-112 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, "circuitry" includes processing circuitry, storage media, network interfaces, input/output devices, and/or the like. In some embodiments, other elements of the apparatus 100 may provide or supplement the functionality of particular circuitry. For example, the processor 102 may provide processing functionality, the memory 104 may provide storage functionality, the communications circuitry 108 may provide network interface functionality, and the like, such that each of the circuitries may be formed by other circuitry components of the apparatus 100.

In some embodiments, the processor 102 (and/or co-processor or any other processing circuitry assisting or otherwise associated with the processor) may be in communication with the memory 104 via a bus for passing information among components of the apparatus. The memory 104 may be non-transitory and may include, for example, one or more volatile and/or non-volatile memories. In other words, for example, the memory may be an electronic storage device (e.g., a computer readable storage medium). The memory 104 may be configured to store information, data, content, applications, instructions, tables, data structures, or the like, for enabling the apparatus to carry out various functions in accordance with example embodiments of the present invention.

The processor 102 may include various processing devices and may, for example, include one or more processing devices configured to perform independently from one another. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 102 may be configured to execute instructions stored in the memory 104 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 100 may include input/output circuitry 106 that may, in turn, be in communication with the processor 102 to provide output to the user and, in some embodiments, to receive an indication of a user input. The input/output circuitry 106 may comprise a user interface and may include a display and may comprise a web user interface, a mobile application, a client device, a kiosk, or the like. In some embodiments, the input/output circuitry 106 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 104, and/or the like). The input/output circuitry 106 may provide a mechanism for a user to enter clinical findings on a clinical report and/or on a clinical diagram (e.g., a mouse, keyboard, or the like) and to provide for display of the clinical report and/or clinical diagram (e.g., via a monitor or other display).

The communications circuitry 108 may be any means such as a device or circuitry embodied in either hardware or a combination of hardware and software that is configured to receive and/or transmit data from/to a network and/or any other device, circuitry, or module in communication with the apparatus 100. In this regard, the communications circuitry 108 may include, for example, a network interface for enabling communications with a wired or wireless communication network. For example, the communications circuitry 108 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The clinical reporting circuitry 110 may include hardware configured to receive and/or generate clinical reporting information for a patient. In this regard, the clinical reporting circuitry 110 may include one or more application-specific interface circuits designed to, or a configured processor, such as the processor 102, programmed with one or more clinical reporting algorithms to, facilitate the generation of clinical reports based on user input related to an analysis of a patient.

The image editing circuitry 112 may include hardware and/or software configured to present a clinical diagram for editing. In this regard, the image editing circuitry 112 may include one or more ASICs or configured processors that are configured to apply edits to a clinical diagram based on user input directly to the clinical diagram, or via user input to the clinical report corresponding to the clinical diagram. The image editing circuitry may generate, from user input, a change to a clinical diagram that is representative of the user input into the clinical diagram or the clinical report in such a way as to accurately depict the edits provided by the user, while minimizing the effort required on behalf of the user to fully detail the edits needed. In this manner, the image editing circuitry is configured to interpret findings in the clinical report or otherwise entered by a user to make changes to the clinical diagram.

As will be appreciated, any computer program instructions and/or other type of code may be loaded onto a computer, processor or other programmable apparatus's circuitry to produce a machine, such that the computer, processor or other programmable circuitry that executes the code on the machine creates the means for implementing various functions, including those described herein.

As described above and as will be appreciated based on this disclosure, embodiments of the present invention may be configured as methods, mobile devices, backend network devices, and the like. Accordingly, embodiments may comprise various means comprised entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Having now described an apparatus configured to implement and/or support implementation of various example embodiments, features of several example embodiments will now be described. It will be appreciated that the following features are non-limiting examples of features provided by some example embodiments. Further, it will be appreciated that embodiments are contemplated within the scope of this disclosure that implement various subsets or combinations of the features further described herein. Accordingly, it will be appreciated that some example embodiments may omit one or more of the following features and/or implement variations of one or more of the following features.

Embodiments provided herein include a reporting platform with a visualized diagram/model that improves the user experience both by the ability to view and understand the procedure findings and the ability to enter data in a more efficient manner. Embodiments provide a user interface for entering data in a text-based clinical report and provide a visual interface through which a diagram can be graphically modified to depict clinical findings, which are then translated and populated within the text based clinical report.

FIG. 2 illustrates an example embodiment of a user interface for a clinical report according to an example embodiment of the present disclosure. As shown, the user interface 200 includes information identifying a patient 210 that is the subject of the clinical report. The user interface 200 may further include procedure information 220 relating to the patient, procedure staff (e.g., a surgeon or technician performing a procedure) 230, indications 240, and risk factors 250. In this user interface, a physician my enter information relating to the patient and the available information fields as appropriate. A procedure type may be selected via a menu available at 260. The selected procedure may cause the retrieval of a diagram relating to the procedure. The diagram may be a new, generic diagram associated with a patient's body region relating to the procedure, or may be a previously modified diagram of the specific patient's body region if the patient has been through a procedure on the same body region in the past.

FIG. 3 illustrates an example embodiment of a clinical diagram associated with a specific procedure. In the instant embodiment, the diagram is for a procedure relating to the carotid arteries that carry blood to the head and neck and their main branches. This procedure 260 is depicted as selected in the clinical report template 200 of FIG. 2. The selection of the carotid procedure type in the template 200 may retrieve the clinical diagram illustrated in FIG. 3, while selections of different procedures may retrieve a different clinical diagram associated with the selected procedure. According to the clinical diagram 300 of FIG. 3, no prior procedures or clinical findings have been entered for the clinical report, such that the clinical diagram 300 of FIG. 3 is generic and depicts a typical carotid system, which provides a basis for clinical findings and any revisions/changes to the clinical diagram.

The clinical diagram 300 of FIG. 3 is constructed of a plurality of segments to form the arteries of the carotid system 340. As shown, the left and right common carotid arteries 320 are shown together with the left and right vertebral arteries 330 and the left and right external carotid arteries 310 and internal carotid arteries 305. The illustrated arteries are formed of a plurality of segments, which facilitates the addition of anomalies within the arteries as will be discussed further below. Vessels may be the main building block of the vascular clinical diagram divided into segments as described further below. Each anatomical finding in the clinical report and diagram relates to a vessel segment. Each vessel segment may include unique identifying information, wherein the identifying information includes a function of the segment (e.g., vein, artery, AV fistula, etc.) and a position within the vascular system. This unique identifying information may be used to correlate the individual vessel segments with the clinical report, and to inform the vascular diagram for connectivity purposes between segments. The vessels may be presented in color, where an artery presented in a first color (e.g., red) can only contain artery related clinical findings, such as a graft, while a vein may be presented in a second color (e.g., blue) and can contain only vein related clinical findings such as a thrombosis.

The arteries and veins may be generated with a vessel architecture where splines are generated that represent the edges of the vessel segment, with lines closing in the segment to be connected to other vessel segments. FIG. 4 illustrates an example vessel segment 345 including cardinal splines 350 and 360 forming the curvature of the vessel segment 345, with lines 355 forming the ends of the vessel segment. Vessel segments may be connected to structure data to form a clinical diagram by assigning each segment a relevant segment ID. Embodiments create a clean connection between segments without requiring a designer or clinician to be entirely precise by using a connectivity algorithm to find the nearest segment through segment hierarchy and proximity, and use this connectivity algorithm to create an actual connection between the segments, even if they were manually located offset from one another. Segment metadata may further include shape information.

The hierarchy used for the connectivity algorithm may compensate for inaccurate or ambiguous placement of a vessel segment in a diagram. For example, when an artery overlaps a vein, and a segment is placed in proximity to the overlapping vessels, it is imperative to understand to which vessel the segment should be connected. The vessel properties may provide an indication of whether the segment should be connected to an artery or a vein, such that the hierarchy includes context awareness. Embodiments described herein may store a hierarchy table for veins and for arteries to resolve other connectivity issues. A similar process may be used for adding a graft as described below.

FIG. 5 illustrates a connection made between two segments 345 and 365 using a vessel connectivity algorithm. When segment 365 is placed in proximity to segment 345, the segment 365 connects to segment 345 on a side of segment 345. A four-point spline (with points 343, 367, 369 and 349) replaces the three-point spline (with points 343, 347 and 349) by replacing the middle control point 347 with two points 367 and 369 of the connecting segment 365. At a rendering stage, the four point spline is converted to three Bezier curves (371, 372 and 373), with the middle Bezier curve 372 between the vessel segments replaced with a line 374 ending segment 345, as with the end lines 355 of the segment 345 of FIG. 4.

Using mathematical calculations on a segment's shape which is built from the cardinal splines and lines described with respect to FIGS. 4 and 5, clinical findings can be placed into or removed from a segment. Referring back to FIG. 3, the clinical diagram is made up of a plurality of these segments, and each segment may be separately addressed to render findings of the respective segment. Embodiments of the clinical diagram described herein may include at least three types of clinical findings: Coverage; Pattern; and Connector.

FIG. 6 illustrates an example embodiment of clinical findings added to the clinical diagram. These findings may be added using a user interface graphical tool on the clinical diagram 300, such as by selecting an option from a tool bar 410 that includes the different types of clinical findings. As shown, options may include blockages to be shown on both sides of a vessel 415, blockage to be shown on one side of a vessel 420, and stent placement/coverage 425. In the example embodiment of FIG. 6, stent placement 435 (a pattern) is shown across several vessel segments of the carotid artery. This stent placement 435 can be inserted in the clinical diagram 300 by user interface with the diagram through selection of the stent clinical finding menu option 425, and selection of corresponding vessel segments in which to place the stent pattern. Placement of the stent in the clinical diagram may automatically add textual clinical findings corresponding to the stent and the placement within the artery in the clinical report without requiring a physician to manually enter the description of the clinical finding. Optionally, a stent can be selected and placement identified on the clinical report, whereby the stent may be generated on the clinical diagram 300 in a similar manner. Further, if the stent is selected and placed through the clinical report, the clinical diagram 300 may be used to interface with the stent and modify or revise the stent coverage graphically for accuracy.

FIG. 7 illustrates a clinical finding involving "coverage", where plaque or stenosis is added to the clinical diagram. As with the stent, the plaque or stenosis can be added graphically to the clinical diagram 300. The coverage 450 is added on top of a segment using mathematical calculations applied to the shape of one or more segments. While plaque is drawn inside a segment, other similar tools may be used to draw stenosis outside of the segment constricting the segment. The algorithm for coverage takes into account that a segment may be connected to another vessel segment as a result of the connectivity algorithm, and may establish coverage of plaque along more than one selected segment. As depicted, the plaque coverage 450 extends along the artery 455 and along branches of the artery 460 and 465. The connectivity algorithm, by virtue of establishing breaks in the cardinal splines for vessel junctions provides basis for the plaque coverage to extend through the vessel junctions without obstructing the vessel junction along the portion of a segment with a removed Bezier curve.

Plaque coverage is also shown in vessel segment 470, with considerably more blockage. When selecting coverage, such as using graphical selection element 415, a percentage of blockage can be specified to identify how much plaque should be shown on the clinical diagram 300. The plaque of 450 may only be 20% blockage, while the plaque of 470 may include 70-90% blockage. This degree of blockage, along with the placement, may be inserted via the graphical user interface as described above, where the findings may then be populated in the clinical report to describe the location of a blockage and the degree of the blockage.

Graphically, adding coverage such as plaque coverage to a clinical diagram is complex. FIG. 8 illustrates a coverage algorithm, where coverage is added to a vessel segment 475 proximate a vessel intersection 480. The coverage of a vessel by plaque is numerically identified by a percentage of blockage, with 100% being a completely blocked vessel. The percentage of blockage is divided by two, and applied to opposing lines/curves representing the blocked vessel. As shown, the blockage 485 extends to the intersection 480 of the vessels, but does not occlude the intersection. Conversely, as the intersection has been produced using new points added to the cardinal spline curve of the vessel 475, the segments of the cardinal spline curve can be individually addressed for a more accurate depiction of the blockage.

FIG. 9 illustrates a Bezier curve segment 490, which may be a segment of the vessel 475, extending between Bezier points b0 and b3. In this illustrated embodiment, the input parameters include points b0, b1, b2, b3, which are control points of the Bezier curve of a segment. Input vectors representing connections of a segment to other segments, L1 and L2, which start from points b0 and b3, respectively. The coverage percent (C) or blockage is also an input, to determine the portion of the vessel to represent as blocked.

From these inputs, the output are points p0, p1, p2, and p3—control points of the Bezier curve of coverage. The algorithm to produce this output includes calculating vectors v1 and v2 from L1 and L2 vectors. V1=L1*0.5*C, V2=L2*0.5*C. The algorithm further calculates control points of the coverage Bezier curve: p0=b0+v2; p1=b1+v2; p2=b2+v1; p3=b3+v1, shown as curve 496.

The third clinical finding is a connector, such as an artery/vein (AV) fistula or a graft. Such a connector can be added to the clinical diagram by a user through the selection of the connector icon 510 of the tool bar 410, and identifying the locations 515 and 520 for the connector 525 shown as a graft, as shown in FIG. 10. An AV fistula is generated in much the same way, though the AV fistula may change the shape of a segment to connect with another segment. An aneurysm may be added to the clinical diagram through selection of the icon 530 and placement in the diagram 300.

Clinical findings, as described above and illustrated in the figures, have specific presentation of each clinical finding displayed in a clear and distinct manner. Using mathematical calculations on a vessel segment shape which has been built from cardinal splines and lines, clinical findings can be placed in and out of the segment. This enables placement of clinical findings without requiring prior understanding of the actual shape of the vessel.

Entering clinical findings in the user interface may generate a graphical element within the diagram. Optionally, a user may manipulate the diagram through adding of features which, in turn, adds textual data to the report corresponding to the added features, such as blockages, stent placements, plaque, etc. Embodiments described herein include a plurality of predefined diagrams; however, users can create custom diagrams based on a patient's unique physiology. Users can create segments and then give segments identifications (e.g., artery, vessel, etc.). Once segments are generated and identified, the identification and spatial data may inform a clinical report. The clinical diagram may be modified at any point such as to add vessels where they don't exist in the diagram.

Embodiments described herein provide a user-centric approach to clinical reporting and clinical diagramming of a patient's clinical findings. Embodiments provide enhanced functionality and a user-friendly interface promoting enhanced ease of use, data entry and consumption.

Example embodiments include features that render the clinical data easily interpreted and consumed by a physician/technician. These features include a navigation bar designed as a step-by-step flow according to the way a user works. Interactive vascular diagrams enable easy visualization of a patient's condition. Previous procedures and clinical findings can be maintained on a patient-specific clinical diagram/report and be available for future procedures and review. Preliminary results of a procedure, entered via the graphical user interface into the clinical diagram, can be generated into a report automatically. The clinical report may include context-sensitive sentences as suggestions/templates that enable a user to quickly and efficiently enter findings, with pre-defined Normal statements that can be inserted into the clinical report when no abnormal findings exist. FIG. 11 illustrates an example embodiment of a normal statement template, wherein a user may select a normal statement for any or all of a variety of different procedures and body regions. Selecting a normal statement may populate a clinical report in an efficient manner to identify no issues were found without requiring elaborate detail.

The data integrity of the clinical diagram and report may also be improved by example embodiments described herein. Mandatory fields may be configured to be required or to have values entered by the technician. An indication of missing mandatory fields may be presented to a user to enable quick identification of the data required to complete the clinical report.

Embodiments may extrapolate information based on user-provided data in the clinical diagram. Automatic calculations may be performed based on predefined formulas making entering data faster and more accurate. The formula used for calculations may be viewed by hovering over the formula icon on the user interface. The formula can be overridden enabling the user to manually enter a value. According to an example embodiment, certain dimensions of an organ or other tissue may be entered by a user, and based on predetermined formulas, dimensions of other organs or missing dimensions of an organ may be generated with a reasonably accurate estimate. Dimensions measured may be entered into a clinical diagram and extrapolated or calculated as described above, and thus may be entered into the clinical report.

An example embodiment of a generated clinical report is shown in FIG. 12, where the report may be preliminary until finalized by a physician. The report provides data indicative of information entered on the graphical user interface of the clinical diagram. This report may be populated automatically based on the clinical diagram manipulation, and may optionally be manually edited should any information be inaccurate or require change.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus facilitating clinical reporting, the apparatus comprising:
    at least one processor; and
    at least one non-transitory memory including computer program code instructions stored thereon that, when executed by the at least one processor, cause the at least one processor to perform operations comprising:
        presenting, via a user interface, a clinical diagram comprising a depiction of a vascular system, wherein vessels of the vascular system comprise a plurality of vessel segments and wherein each of the plurality of vessel segments is formed from a pair of cardinal splines and end lines between adjacent ends of the pair of cardinal splines;
        receiving, via the user interface, a first user input identifying at least one clinical finding associated with the vascular system;
        modifying the clinical diagram responsive to the first user input to include a visual representation of the at least one clinical finding within the depiction of the vascular system;
        generating a clinical report based on the modified clinical diagram; and
        populating the clinical report with the at least one clinical finding and a location of the at least one clinical finding corresponding to a segment of the plurality of vessel segments.

2. The apparatus of claim 1, wherein each segment of the vascular system comprises unique identifying information, and wherein the identifying information comprises a position of the segment within the vascular system, and a function of the segment within the vascular system.

3. The apparatus of claim 1, wherein the at least one clinical finding comprises at least one of a blockage, a stent placement, or a connector between vessels.

4. The apparatus of claim 1, wherein the clinical diagram is a first clinical diagram from among a plurality of available clinical diagrams, the operations further comprising:
presenting, via the user interface, a list of the plurality of available clinical diagrams; and
receiving, via the user interface, a second user input comprising a selection of the first clinical diagram.

5. The apparatus of claim 1, the operations further comprising:
receiving, via the user interface, a second user input corresponding to a modification of the clinical diagram, wherein the modification comprises a new vessel or connector to be added to the clinical diagram;
receiving an indication of placement of the new vessel or connector in the clinical diagram; and
applying a connectivity algorithm to the new vessel or connector to join the new vessel or connector to an existing segment of the plurality of vessel segments.

6. The apparatus of claim 5, wherein the connectivity algorithm uses proximity of the new vessel or connector to existing segments and a hierarchy of existing segments to establish the existing segment to which the new vessel or connector is joined.

7. The apparatus of claim 6, the operations further comprising:
converting a three point cardinal spline of the pair of cardinal splines of the existing segment to a four point spline responsive to applying the connectivity algorithm, thereby replacing a middle control point of the three point cardinal spline with two points; and
join ends of two splines forming the new vessel or connector to the two points.

8. A computer program product comprising at least one non-transitory computer-readable storage medium having computer-executable program code instructions stored therein, the computer-executable program code instructions comprising program code instructions to:
display, via a user interface, a clinical diagram comprising a depiction of a vascular system, wherein vessels of the vascular system comprise a plurality of vessel segments and wherein each of the plurality of vessel segments is formed from a pair of cardinal splines and end lines between adjacent ends of the pair of cardinal splines;
receive, via the user interface, a first user input identifying at least one clinical finding associated with the vascular system;
modify the clinical diagram responsive to the first user input to include a visual representation of the at least one clinical finding within the depiction of the vascular system;
generate of a clinical report based on the modified clinical diagram; and
populate the clinical report with the at least one clinical finding and a location of the at least one clinical finding corresponding to a segment of the plurality of vessel segments.

9. The computer program product of claim 8, wherein each segment of the vascular system comprises unique identifying information, and wherein the identifying information comprises a position of the segment within the vascular system, and a function of the segment within the vascular system.

10. The computer program product of claim 8, wherein the at least one clinical finding comprises at least one of a blockage, a stent placement, or a connector between vessels.

11. The computer program product of claim 8, wherein the clinical diagram is a first clinical diagram from among a plurality of available clinical diagrams, the computer program product further comprising program code instructions to:
present, via the user interface, a list of the plurality of available clinical diagrams; and
receive, via the user interface, a second user input comprising a selection of the first clinical diagram from the list.

12. The computer program product of claim 8, further comprising program code instructions to:
receive, via the user interface, a second user input corresponding to a modification of the clinical diagram, wherein the modification comprises a new vessel or connector to be added to the clinical diagram;
receive an indication of placement of the new vessel or connector in the clinical diagram; and
apply a connectivity algorithm to the new vessel or connector to join the new vessel or connector to an existing segment of the plurality of vessel segments.

13. The computer program product of claim 12, wherein the connectivity algorithm uses proximity of the new vessel or connector to existing segments and a hierarchy of existing segments to establish the existing segment to which the new vessel or connector is joined.

14. The computer program product of claim 13, further comprising program code instructions to:
convert a three point cardinal spline of the pair of cardinal splines of the existing segment to a four point spline responsive to applying the connectivity algorithm, thereby replacing a middle control point of the three point cardinal spline with two points; and
join ends of two splines forming the new vessel or connector to the two points.

15. A method comprising:
presenting, by a processor and via a user interface, a clinical diagram comprising a depiction of a vascular system, wherein vessels of the vascular system comprise a plurality of vessel segments and wherein each of the plurality of vessel segments is formed from a pair of cardinal splines and end lines between adjacent ends of the pair of cardinal splines;
receiving, by the processor and via the user interface, a first user input identifying at least one clinical finding associated with the vascular system;
modifying, by the processor, the clinical diagram responsive to the first user input to include a visual representation of the at least one clinical finding within the depiction of the vascular system;
generating, by the processor, a clinical report based on the modified clinical diagram; and
populating, by the processor, the clinical report with the at least one clinical finding and a location of the at least one clinical finding corresponding to the user input based on a segment of the plurality of vessel segments.

16. The method of claim 15, wherein each segment of the vascular system comprises unique identifying information, and wherein the identifying information comprises a position of the segment within the vascular system, and a function of the segment within the vascular system.

17. The method of claim 15, wherein the at least one clinical finding comprises at least one of a blockage, a stent placement, or a connector between vessels.

18. The method of claim 15, wherein the clinical diagram is a first clinical diagram from among a plurality of available clinical diagrams, the method further comprising:
   presenting, by the processor and via the user interface, a list of the plurality of available clinical diagrams; and
   receiving, by the processor and via the user interface, a second user input comprising a selection of the first clinical diagram.

19. The method of claim 15, further comprising:
   receiving, by the processor and via the user interface, a second user input corresponding to a modification of the clinical diagram, wherein the modification comprises a new vessel or connector to be added to the clinical diagram;
   receiving, by the processor, an indication of placement of the new vessel or connector in the clinical diagram; and
   applying, by the processor, a connectivity algorithm to the new vessel or connector to join the new vessel or connector to an existing segment of the plurality of vessel segments.

20. The method of claim 19, wherein the connectivity algorithm uses proximity of the new vessel or connector to existing segments and a hierarchy of existing segments to establish the existing segment to which the new vessel or connector is joined.

* * * * *